US008147439B2

(12) United States Patent
Devito (10) Patent No.: US 8,147,439 B2
(45) Date of Patent: Apr. 3, 2012

(54) ANKLE-FOOT ORTHOSIS (76) Inventor: James Devito, Staten Island, NY (US)

(*) Notice: Subject to any disclaimer, the term of this patent is extended or adjusted under 35 U.S.C. 154(b) by 126 days.

(21) Appl. No.: 12/766,770

(22) Filed: Apr. 23, 2010

(65) Prior Publication Data
US 2011/0264023 A1 Oct. 27, 2011

(51) Int. Cl.
A61F 5/00 (2006.01)
(52) U.S. Cl. .......................................... 602/23; 602/27
(58) Field of Classification Search .............. 602/23–27; 128/882
See application file for complete search history.

(56) References Cited

U.S. PATENT DOCUMENTS

| 7,270,644 | B2 * | 9/2007 | Ingimundarson | 602/27 |
| 7,513,880 | B2 * | 4/2009 | Ingimundarson et al. | 602/23 |
| 2004/0186401 | A1 * | 9/2004 | Guenther | 602/16 |
| 2007/0135746 | A1 * | 6/2007 | Korner et al. | 602/27 |

* cited by examiner

Primary Examiner — Michael A. Brown
(74) Attorney, Agent, or Firm — Anna Vishev (57) ABSTRACT An ankle-foot orthosis having a tubular calf brace and a splint. The calf brace is configured to substantially enclose and compress a calf of a patient and includes a front wall, a rear wall and a chute formed at the rear wall. The splint includes a footplate and a stalk extending from the footplate, the stalk being insertable into the chute of the tubular calf brace to removably secure the splint to the tubular calf brace.

11 Claims, 15 Drawing Sheets

ANKLE-FOOT ORTHOSIS

BACKGROUND

Present application generally relates to the field of ankle-foot orthoses.

Figure 1:
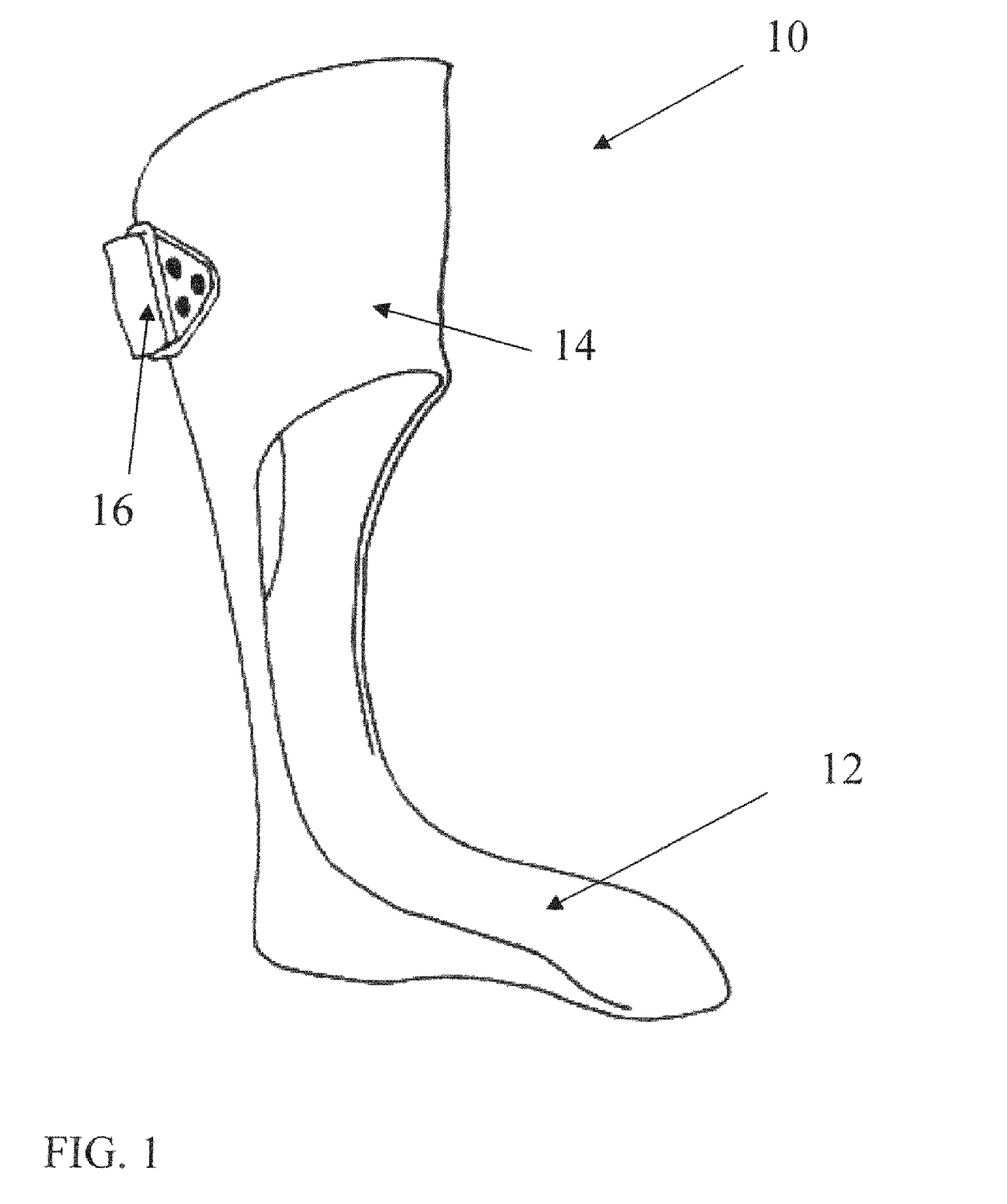
FIG. 1 shows a prior art AFO.
Figure 2:
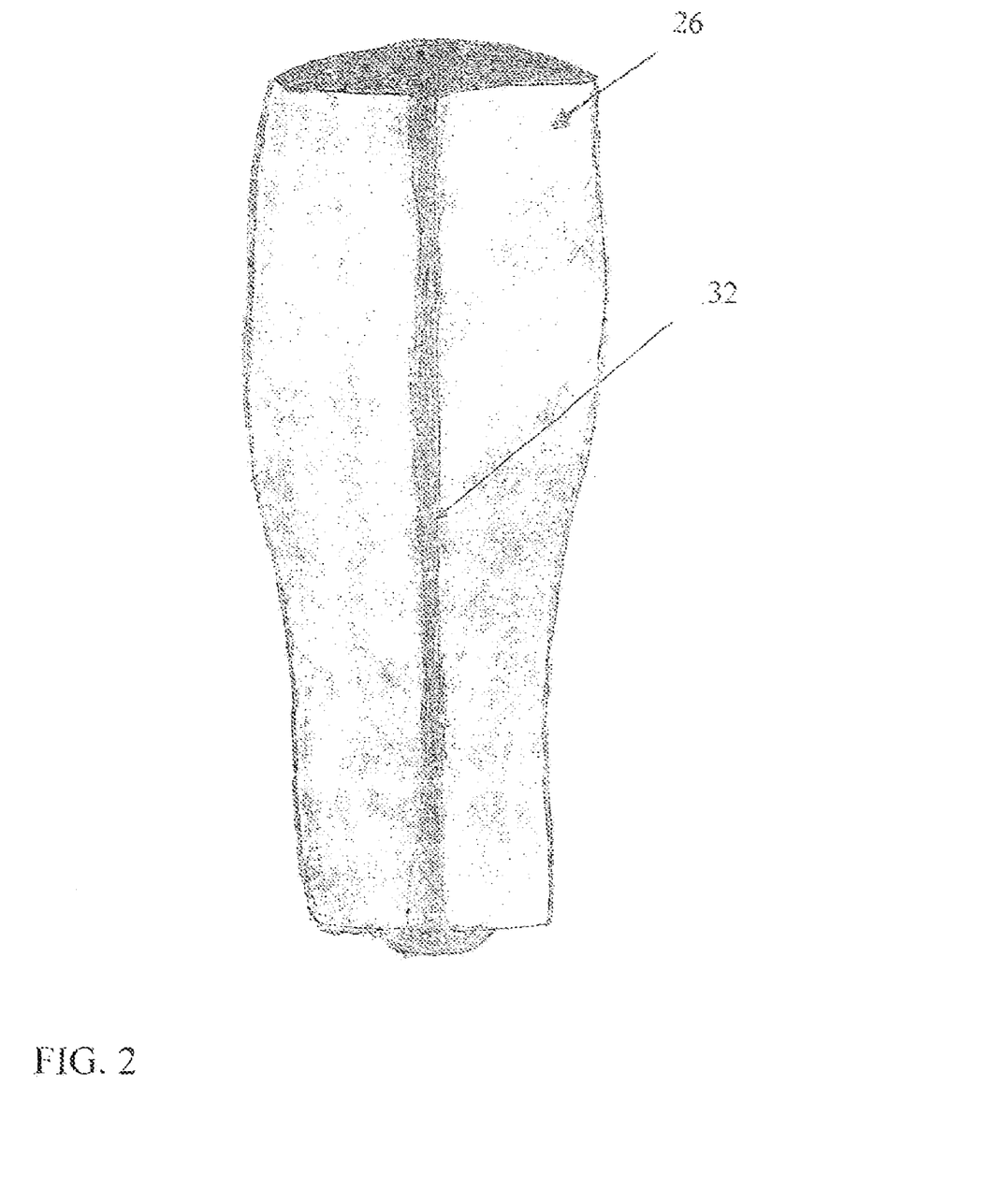
FIG. 2 is a front view of a calf brace of an AFO according to an embodiment of the present invention.

Ankle-foot orthoses (AFOs) are orthoses, or braces, usually plastic, encompassing the ankle joint and all or part of the foot. AFOs are externally applied to control position and motion of the ankle, compensate for weakness, correct deformities, or provide forward flexing, energy loading, and balance control. The orthosis may also be adjusted for size and fit by a prosthesis. A conventional example of an AFO is shown in FIG. 1.

AFOs are commonly used in the treatment of disorders that affect muscle function such as stroke, spinal cord injury, muscular dystrophy, cerebral palsy, polio, multiple sclerosis and peripheral neuropathy. AFOs can be used to provide support to weak or wasted limbs or to position a limb with tight, contracted muscles into a more normal position. They are also used to immobilize the ankle and lower leg in the presence of arthritis or fracture, and to correct Foot Drop, or Drop Foot.

Drop Foot is an abnormal neuromuscular disorder that affects a patient's ability to raise his/her foot at the ankle. A patient experiencing Drop Foot will also be unable to point his/her toes upwards toward the body (dorsiflexion) or move the foot at the ankle inward or outward. The loss of function may also be accompanied by pain, weakness, and numbness. The lack of ability to flex the foot leads to calf muscle atrophy.

Drop Foot makes walking difficult, causing a person to either drag the foot and toes or to engage in a high-stepping walk called "steppage gait." The condition is not a disease, but a symptom of an underlying problem. It is often caused by an interruption in the signal from the brain to the peroneal nerve. This nerve runs along the outside of the lower leg below the knee. People with amyotrophic lateral sclerosis (ALS), multiple sclerosis (MS), Parkinson's Disease, spinal cord injuries, traumatic brain injuries, cerebral palsy, nerve damage, crushed peronial nerves, tragic accidents, loss of or damaged Gastrocnemius or Soleius muscles, and stroke may experience the effects of the condition, creating a need for an AFO.

The atrophied muscle creates low self-esteem, low self-confidence, leads to feelings of embarrassment. As a result, a patient will wear long pants, not participate in outdoor activities and otherwise limit their enjoyment to conceal an AFO.

SUMMARY

In one general aspect, the present invention is an AFO providing increased support, functionality and comfort over the prior art. A calf brace wraps around an entire periphery of a patient's calf and is, closed via some attachment means, such as a zipper. An internal cavity, or chute, is located inside the calf brace and positioned at its rear center, to accept a stalk portion of a splint with a foot and ankle support. In this way, there is no scraping of the AFO against the skin, thereby avoiding the skin irritation and rashes normally associated with prior art AFOs.

According to another aspect of the preferred embodiment, a stocking worn over the calf but under the calf brace prevents contact between the calf and the calf brace. In addition, a sock worn over the foot, with an opening at its rear center, for the stalk to pass through, prevents foot-to-AFO contact. In this way, an AFO system is realized where there is no skin-to-AFO contact.

The brace is open at its front so that the brace can be wrapped around a calf. Each patient's calf brace is individually constructed so as to have a length and thickness fit individually to the length of the patient's leg and the size of the patient's calf.

The leg is tightly secured within the calf brace which is then zipped up. The zipper is preferably a water resistant vinyl zipper. The length of the zipper is determined in accordance with the length of the patients lower leg. The zipper is preferably sewn into the calf brace.

The calf brace provides comfort, realism, protection from external dangers, longevity of the product and does not cause any irritation from the plastic portion of the AFO that runs through the rear of the calf.

In accordance with a further aspect, the present invention provides an AFo which effectively hides the fact that the patient is wearing the device. Specifically, the calf brace is shaped as a normally-formed calf and hides noticeable and fragile plastic parts of the AFO, e.g., the splint.

It is an object of the present invention to provide a calf brace which is extremely light-weight and which provides a tight fit and compression. A mold of the patient's lower leg is made by a prosthesis and the calf brace is sculpted to resemble the shape of a calf.

The above aspects, advantages and features are of representative embodiments only. It should be understood that they are not to be considered limitations on the invention as defined by the claims. Additional features and advantages of the invention will become apparent in the following description, from the drawings, and from the claims.

BRIEF DESCRIPTION OF THE DRAWINGS

The invention is illustrated by way of example and not limitation and the figures of the accompanying drawings in which like references denote like or corresponding parts, and in which.

DETAILED DESCRIPTION OF THE PREFERRED EMBODIMENT AND THE DRAWINGS

Referring to FIG. 1, a prior art AFO is shown, generally indicated by reference numeral 10. A foot plate 12 and a leg support 14 are constructed as a single piece. The piece is secured to a leg by a strap 16.

As shown in FIG. 1, conventional ankle foot orthoses are plastic molded devices supported by at least one strap typically located under the knee area or at the mid-calf of a patient. Most AFOs are weak and provide no protection to an atrophied calf. Further, all AFOs having the strap attachments create irritations to the skin. Each step creates friction, as the strap slides up and down, rubbing against the patient's skin.

Further, once the strap is adjusted, it will secure only one portion of the AFO to the leg, i.e., the portion where the strap is positioned. However, for most people, the calf is thicker at the top than the bottom. Therefore, when the AFO is secured with the strap to the top of mid-portion of the calf, the bottom portion of the AFO becomes extremely unstable because the thinner parts of the calf are not secured to the AFO. Accordingly, as the patient walks, the AFO slides up and down and side-to-side along the leg, aggravating the skin and causing rashes, lesions, blisters, and, possibly, infection. Moreover, because such loosely fit AFO is unstable, it provides little help when walking. Therefore, a patient cannot walk for long periods of time.

Figure 11:
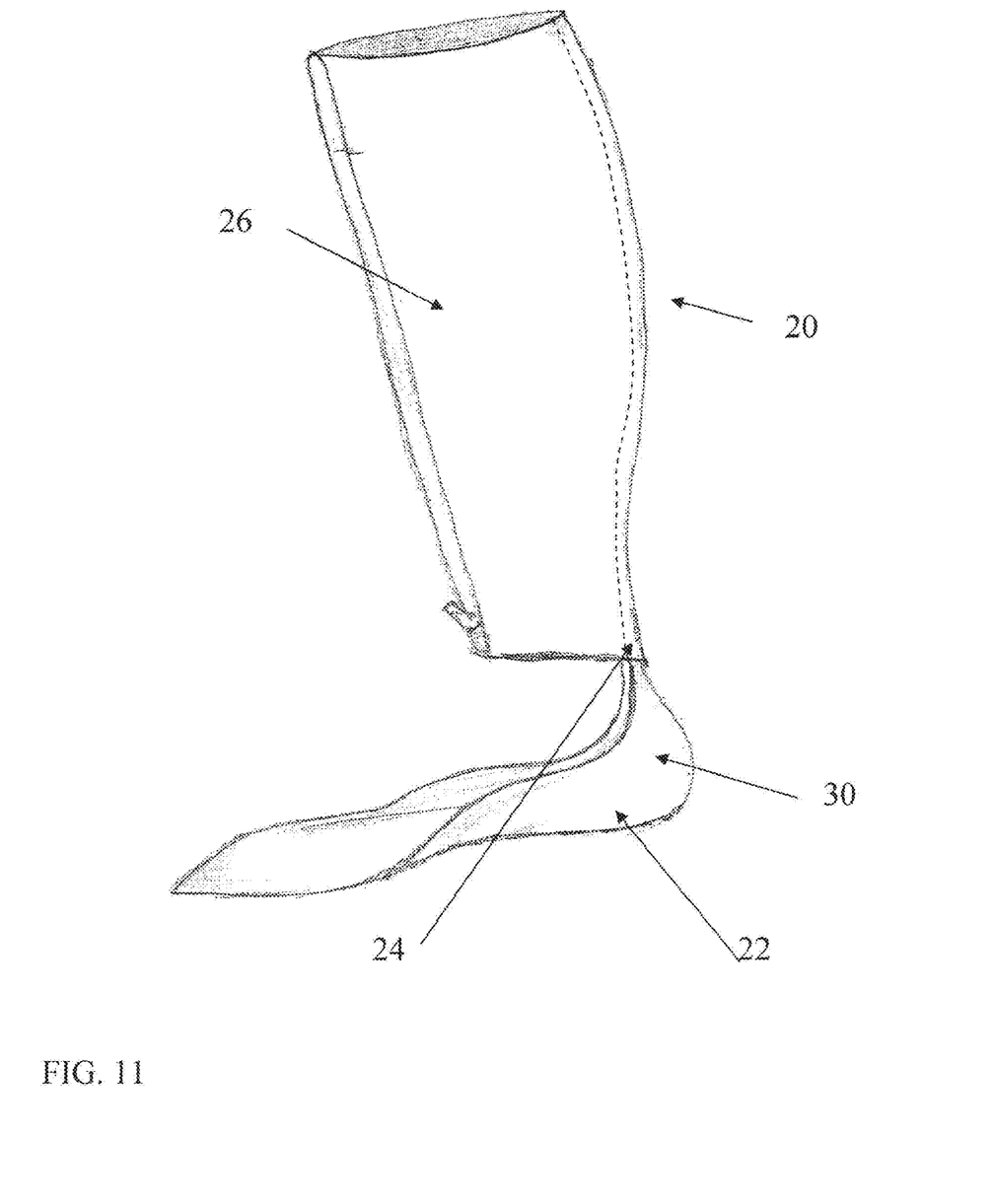
FIG. 11 shows a combination of the calf brace with the stalk and the foot plate in accordance with an embodiment of the present invention.

Referring now to FIG. 11, an AFO according to an embodiment of the present invention is shown, generally indicated by reference numeral 20. A foot plate 22 and a stalk 24 form a single, unitary piece, referred to herein as a splint 30. The splint is removably attached to a calf brace 26 by inserting the stalk 24 into an internal cavity or chute 32 (shown in more detail in FIGS. 4 and 6) of the calf brace 26.

As shown in FIGS. 2 and 3a-3c, calf brace 26 is a substantially tubular member which includes a vertical split opening 32 along the entire length of its frontal face. As discussed later, a closure means, such as a zipper, attaches one side of the opening to the other so that the brace fits snugly over a human calf.

Any utilized closure means seals the calf brace. This tight seal will act as a compression for the leg. Presently there are compression socks that patients use alone or in conjunction with an AFO in order to give support to the venous and lymphatic systems of the leg or patients with diabetes. With the use of the presently disclosed calf brace, the need for such compression socks is eliminated.

As further described below, the tension of the compressed calf brace ensures that the splint does not slide easily out of the chute.

Generally, the calf brace 26 is constructed with a lightweight and sturdy material, like a foam or plastic, formed in the shape of a normal, healthy human calf and upper ankle. The brace 26 may be constructed as a single, unitary piece. Alternatively, the brace 26 may be constructed in layers, as described below. It should be noted that anywhere a layered construction is shown, the layers may all be substituted with a rigid or semi-rigid plastic or foam in a single unitary piece.

Plastazote is one type of suitable foam. The calf brace interior is formed after casting a mold of a human leg for a customized fit, ensuring a sufficiently snug fit to provide compression of the area for circulatory benefits and mechanical support for improved motor function. The exterior surface is shaped to represent a healthy, normal calf muscle proportionate to the size of a particular patient.

Figure 3A:
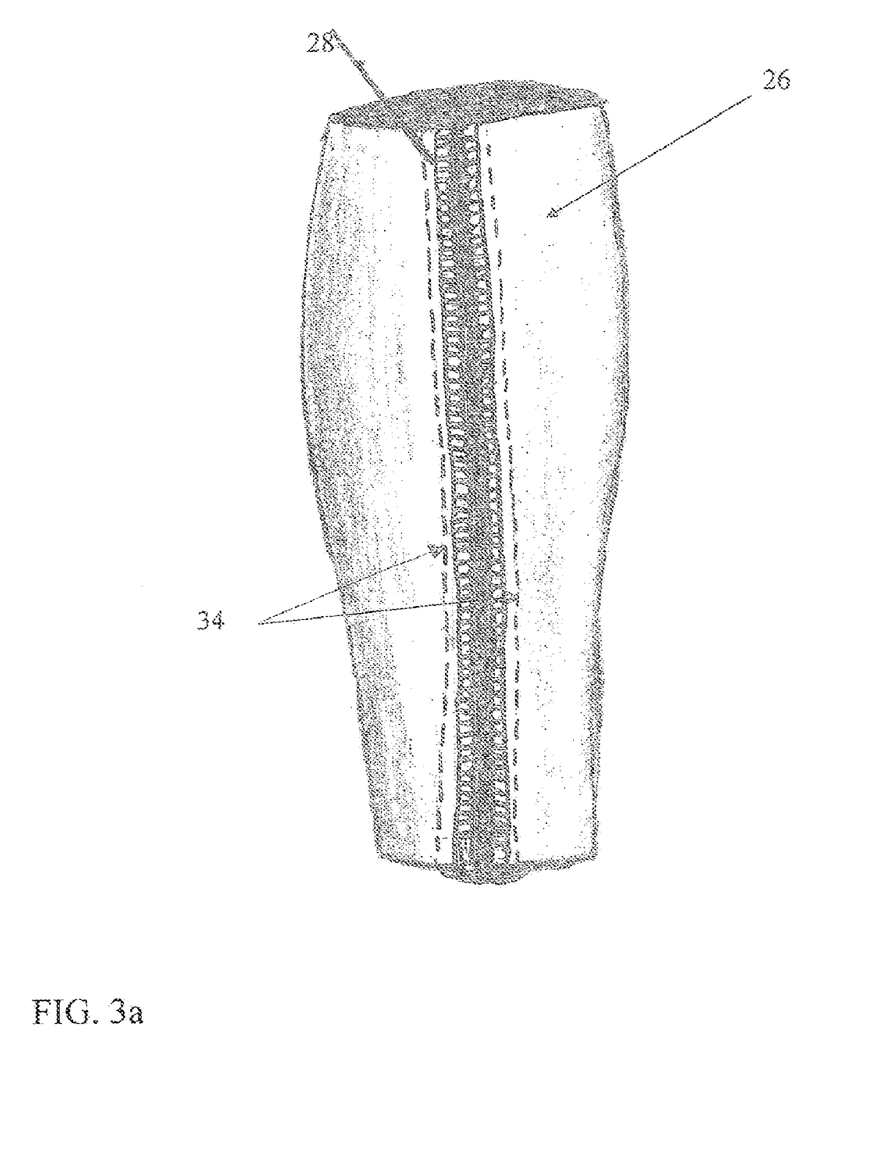
FIG. 3a is a front view of a calf brace part of an AFO according to an embodiment of the present invention, with a standard water proof nylon zipper.

Referring to FIG. 3a a zipper 28 is sewn into the brace 26, along its two edges 34. When the brace is wrapped around a calf, and the zipper 28 is closed, the brace becomes extremely stable and secured to the lower leg. The brace 26 compresses the calf to provide support to the lower leg, as is needed for an atrophied calf.

Figure 3B:
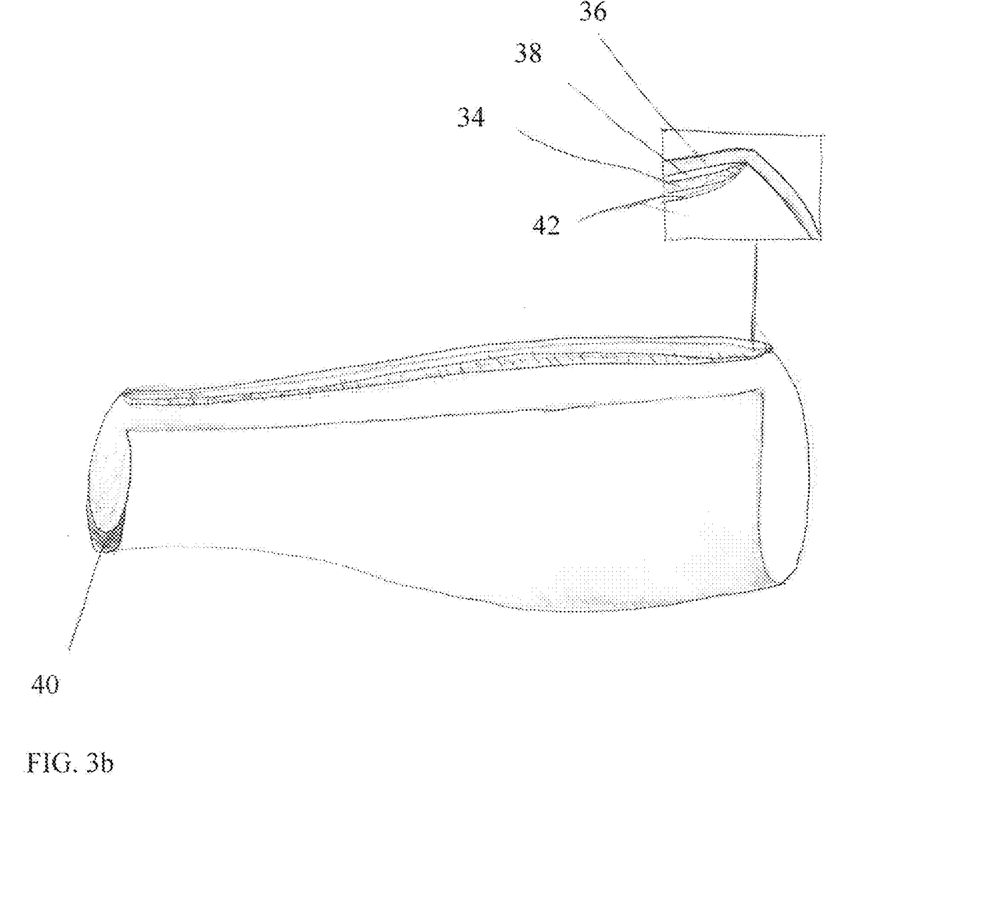
FIG. 3b is a side perspective view of the brace of FIG. 3a with a cut-out view of the zipper portion.
Figure 3C:
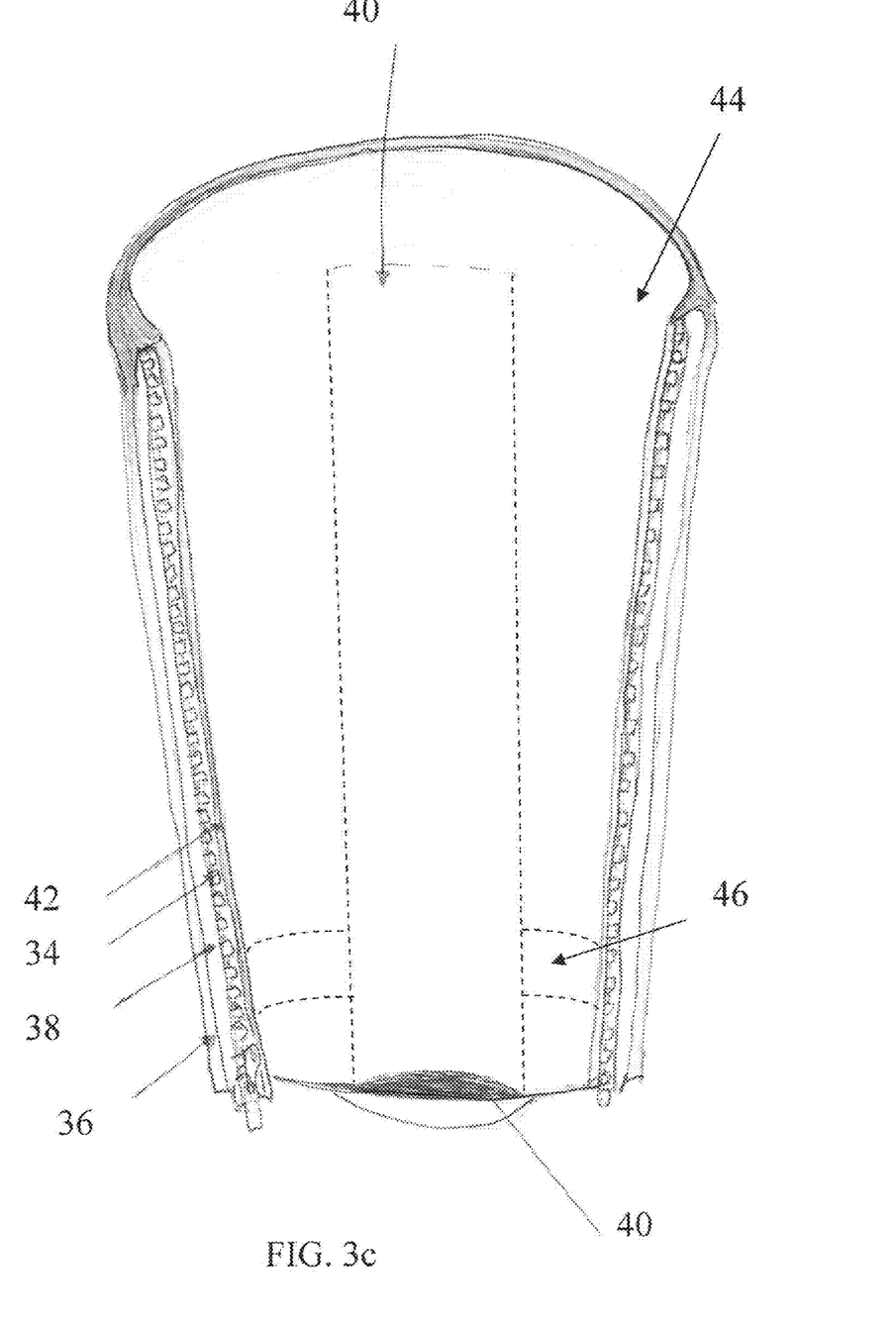
FIG. 3c is a front perspective view of the AFO of FIG. 3a in an open position.

FIGS. 3b and 3c show the calf brace 26 according to a preferred embodiment of the present invention constructed in layers. A first, outer layer is a silicon cover 36 attached to the outer side of a foam or plastic layer 38. The cover 36 can be made to match the tone of human skin to be more aesthetically pleasing and make it appear as if no brace is present when worn.

Along the opening 32, the foam or plastic layer 38 is sandwiched between the outer silicone cover 36 and one of the zipper edges 34. Preferably, a silicone cover re-enforcement 42 is attached to the interior surface of the calf brace 26, thus forming the inner cavity 44 of the calf brace. Because the calf brace is designed for a specific patient, the inner cavity 44 is shaped to correspond to the outer surface of the patient's calf. The layers are preferably attached to each other by an adhesive. Other means of attachment may also be utilized.

Figure 12:
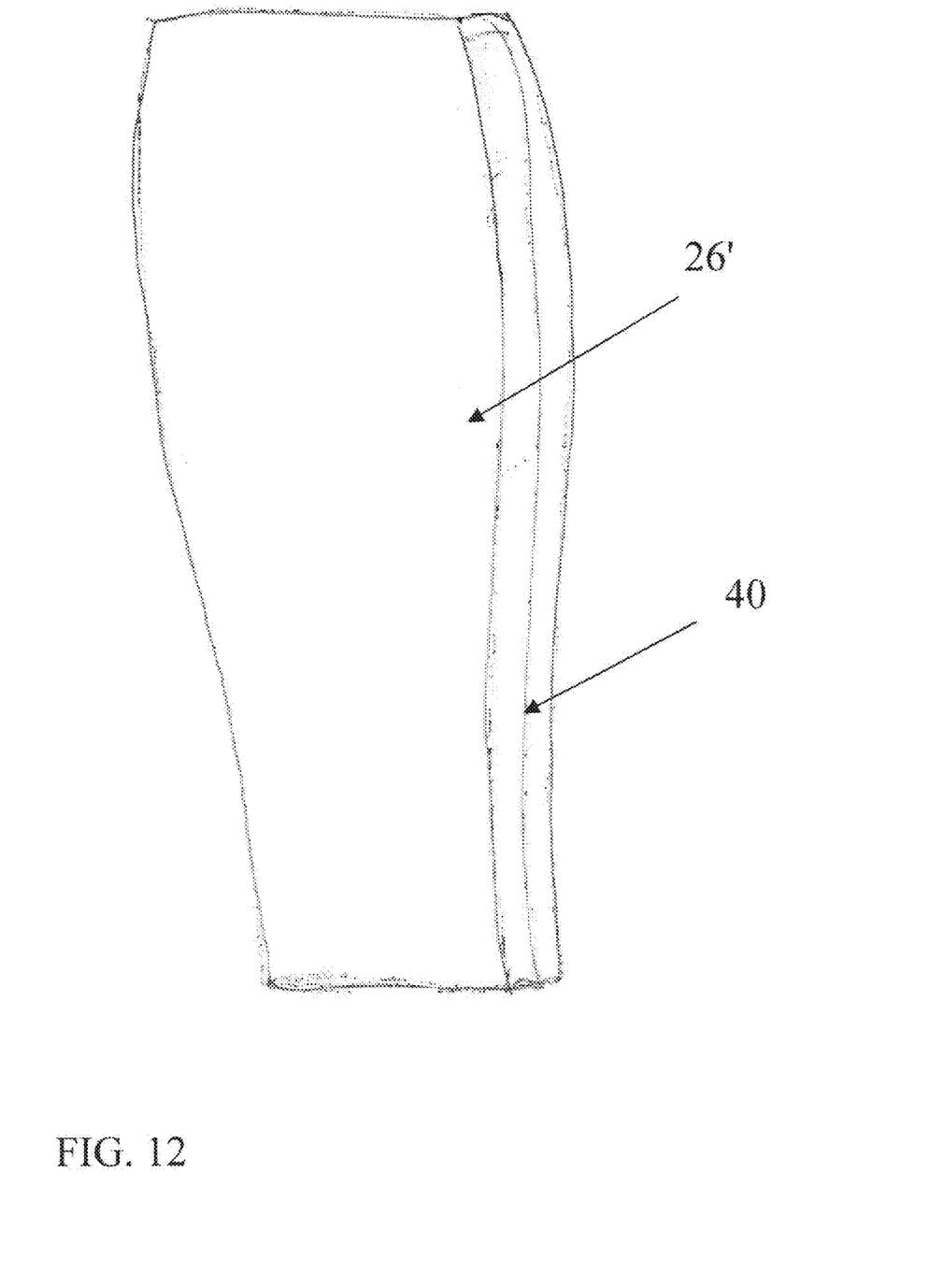
FIG. 12 shows an alternative embodiment of the calf brace.

An alternative embodiment of the calf brace 26' is shown in FIG. 12. In accordance with the alternative embodiment, calf brace 26' is formed as a compression sleeve, preferably formed of a stretchable material, for example, spandex. The chute 40 is then sewn along the rear face of the compression sleeve and used for insertion of the stalk 24 of the splint 30 in the same manner as described below. This alternative embodiment of the calf brace is particularly suitable for people without any deformations in the calf area but still in need of foot and ankle support.

As shown in FIG. 3c, the entrance to the internal chute 40 of the calf brace 26 is positioned at the back of the brace 26. As further shown in FIG. 4, chute 40 receives the stalk portion 24 of the splint 30, thereby, removably attaching the foot plate 22 to the calf brace and providing a rigid structure for foot and ankle support. When the calf brace is constructed in accordance with the multi-layer design described above, the chute is preferably formed within the foam or plastic layer 38.

Figure 4:
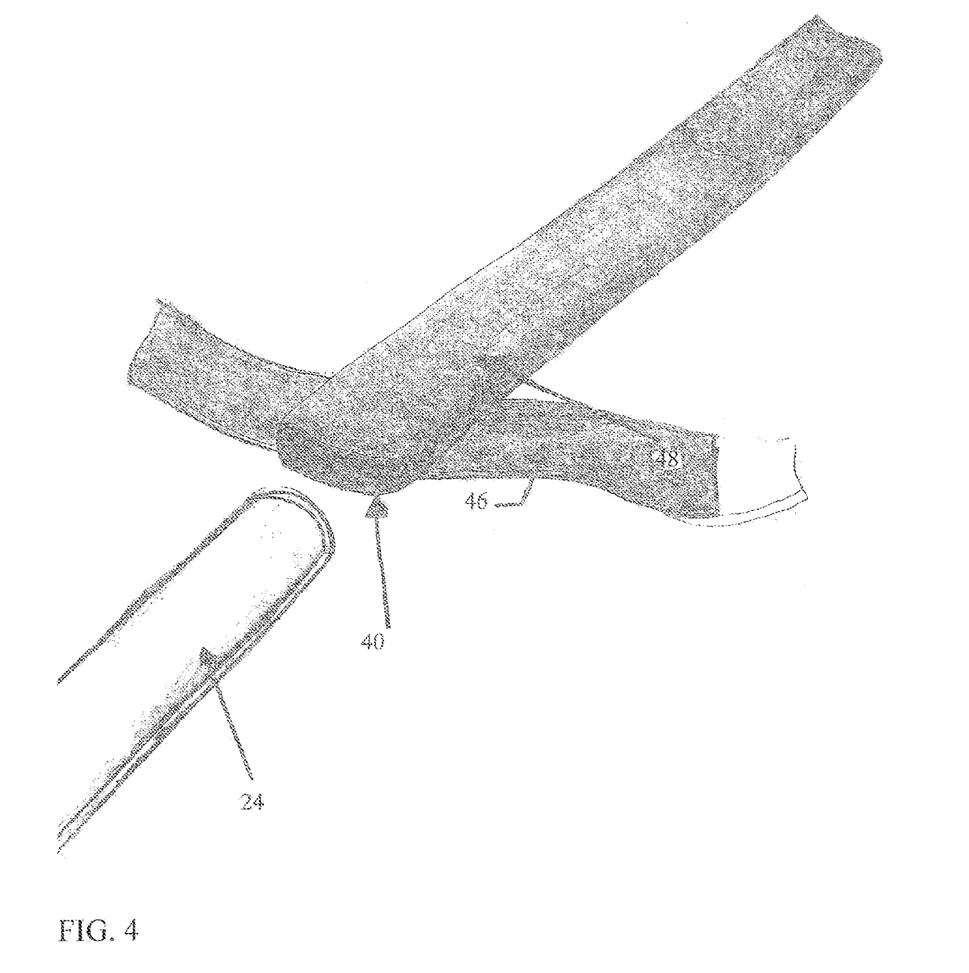
FIG. 4 is a cut-out view of a chute and a reinforcement strip formed in an AFO according to an embodiment of the present invention.

Referring to FIG. 4, further detail of the internal chute 40 is shown. In the preferred embodiment, the interior surface of the chute 40 is formed from a material other than the foam or plastic layer 38. A material resistant to erosion by friction, such as a heavy-duty Polyethylene terephthalate (PET), more commonly known by its trade name Dacron™, is suitable.

A sleeve 48 is formed from the PET and is inserted into the chute 40 of the calf brace. The length of the chute 40 should be slightly less than the height of the calf brace 26 and slightly greater than the length of the stalk 24, to accommodate the stalk. Further, the chute 40 is enclosed at its upper end to prevent the stalk from going through the brace 26 completely. The chute 40 with its inner sleeve 48 is pliable and is positioned inside and at the rear of the calf brace 26. The chute 40 allows the plastic stalk 24 to slide inside the foam or plastic layer 38 and prevents skin contact with the splint stalk 24, thereby preventing skin irritation and rashes commonly associated with prior art AFOs.

As further shown in FIGS. 3c and 4, an reinforcement strip 46 is preferably provided inside the calf brace 26. Reinforcement strip 46 is preferably positioned adjacent a lower portion of the chute 40 and provides additional stability to the device when the stalk 24 is inserted into the chute 40.

Figure 5:
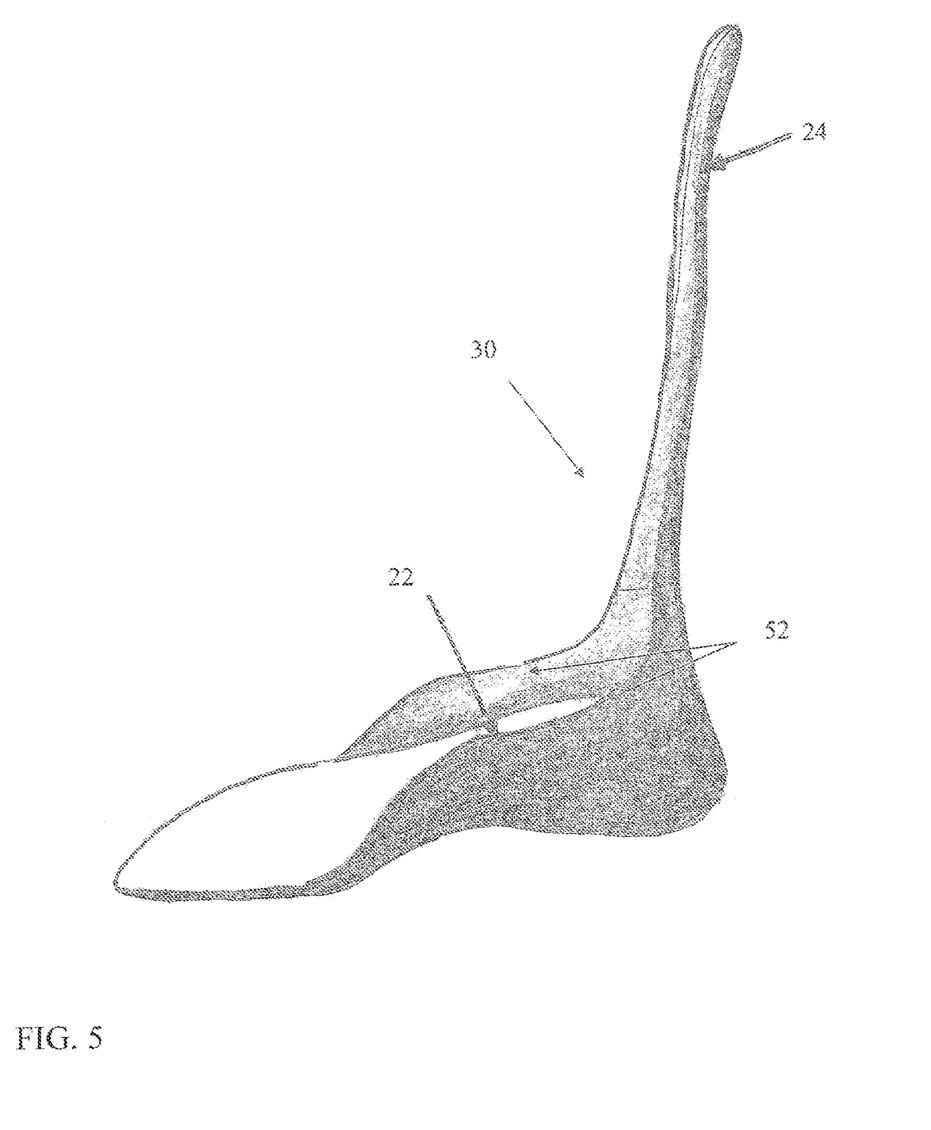
FIG. 5 is a side perspective view of a splint with a foot support provided in an AFO according to an embodiment of the present invention.

Referring to FIG. 5, the splint 30 according to an embodiment of the present invention includes the stalk 24 and the footplate 22 fixedly attached or integrally formed with each other. As explained above, stalk 24 is removably inserted into the chute 40, which, in turn, is affixed into the calf brace 26, thus removably and securely attaching the footplate 22 to the calf brace 26. The footplate may be dimensioned to fit either the left foot or the right foot exclusively.

A footplate sidewall 52 extends upwardly from the footplate 22. The sidewall 52 may be located on either the medial or lateral part of the footplate 22 as is customary with AFOs. There may be two sidewalls 52 extending upwardly from the two side edges of the footplate as well. These sidewalls help to prevent the foot from moving left or right in a transverse plane.

Figure 6:
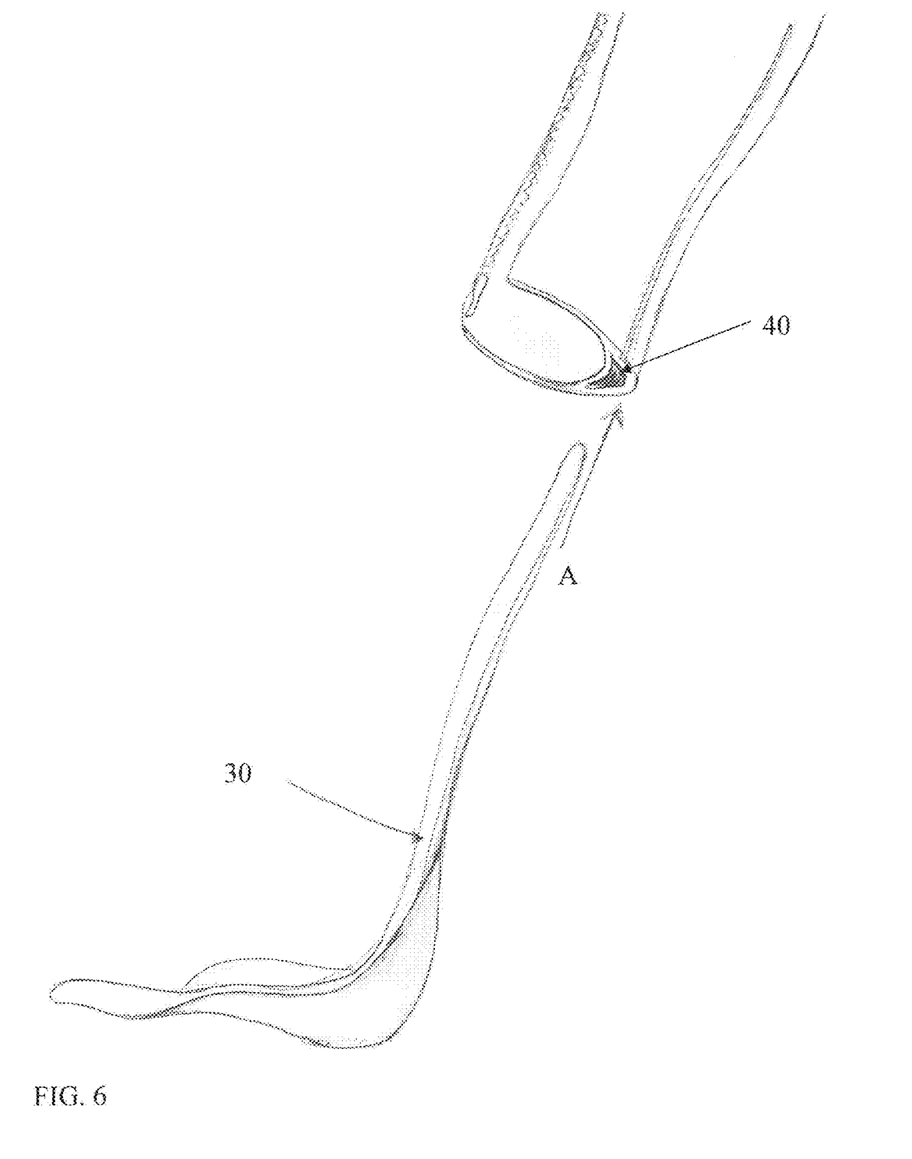
FIG. 6 shows a splint being inserted into a chute of a calf brace according to an embodiment of the present invention.

Referring to FIG. 6, the stalk 24 is inserted in the direction A into the opening of the chute 40 located in the calf brace 26. The tension of the curved splint secures the splint within the chute and prevents the splint from sliding out of the chute easily.

Figure 7:
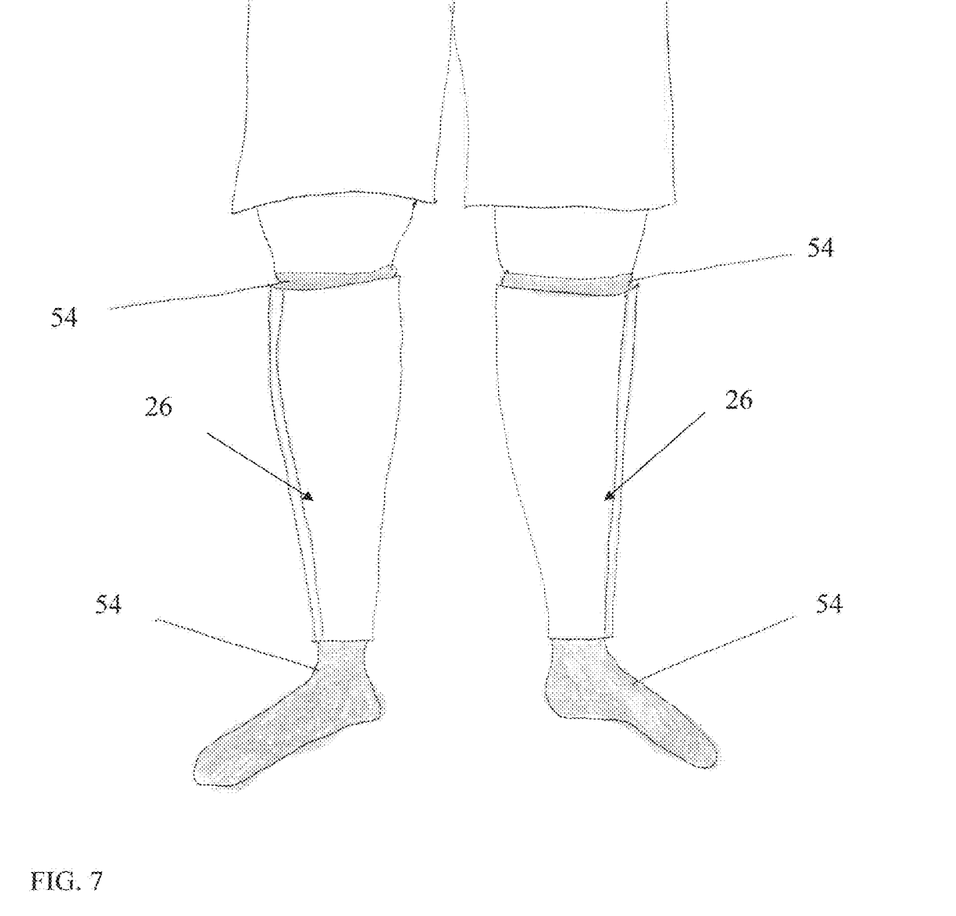
FIG. 7 shows calf braces positioned on patient's legs over stockings.

In use, the patient would preferably first put on an elastic stocking 54 to further protect the skin, then position the calf brace 26 on the leg and secure the zipper 28 to snugly compress the leg within the calf brace. As shown in FIG. 7, stocking 54 is preferably longer than the calf brace 26 to provide skin protection at the top and bottom edges of the brace. The stocking 54 absorbs any sweat that may be produced as a result of wearing the calf brace 26 as well as increases comfort. Stocking 54 is preferably made of nylon or other similar elastic material.

Figure 8A:
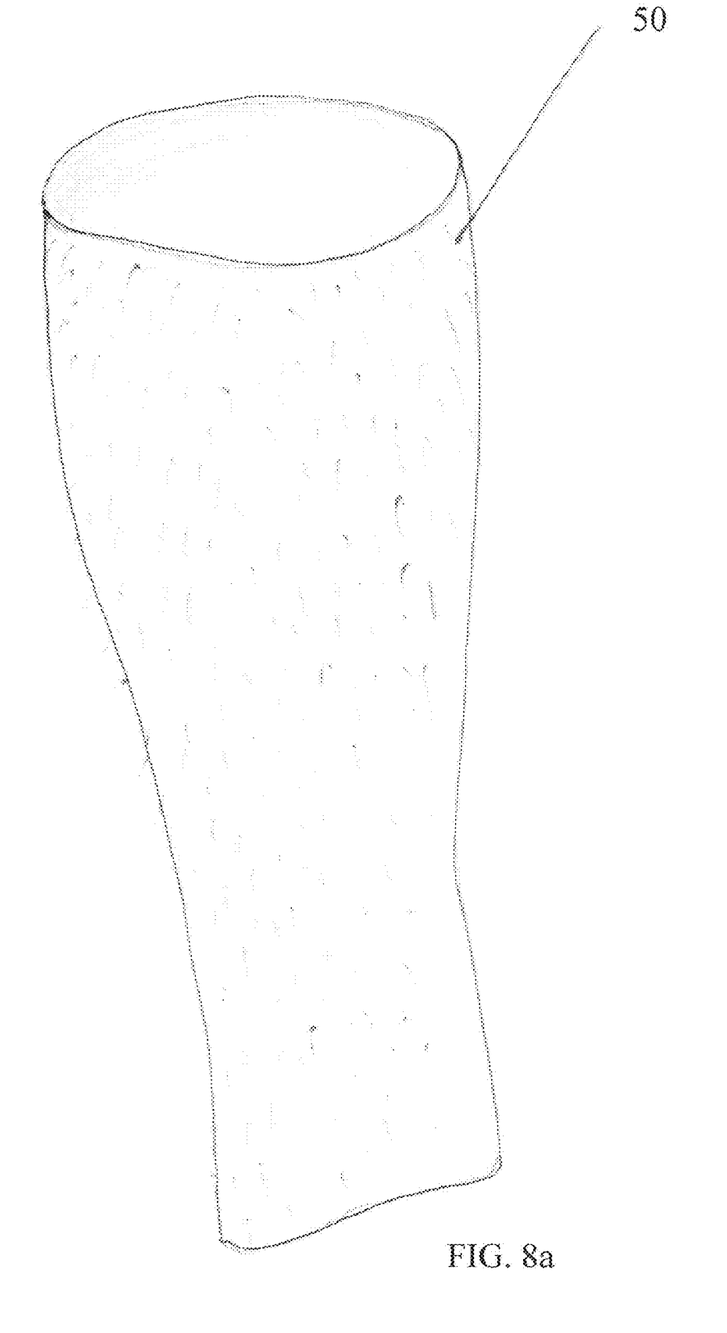
FIG. 8a shows a skin according to an embodiment of the present invention.

Referring to FIG. 8a, according to certain aspects of the present invention, an optional skin cover 50 is provided to mimic the appearance of real human skin and hair. These skins are well-known and used where a patient has suffered extensive damage to the skin, as is the case with burn patients. The cover 50 can be placed over the brace 26 when worn, thus hiding the AFO to make it appear as if nothing were on at all.

Figure 8B:
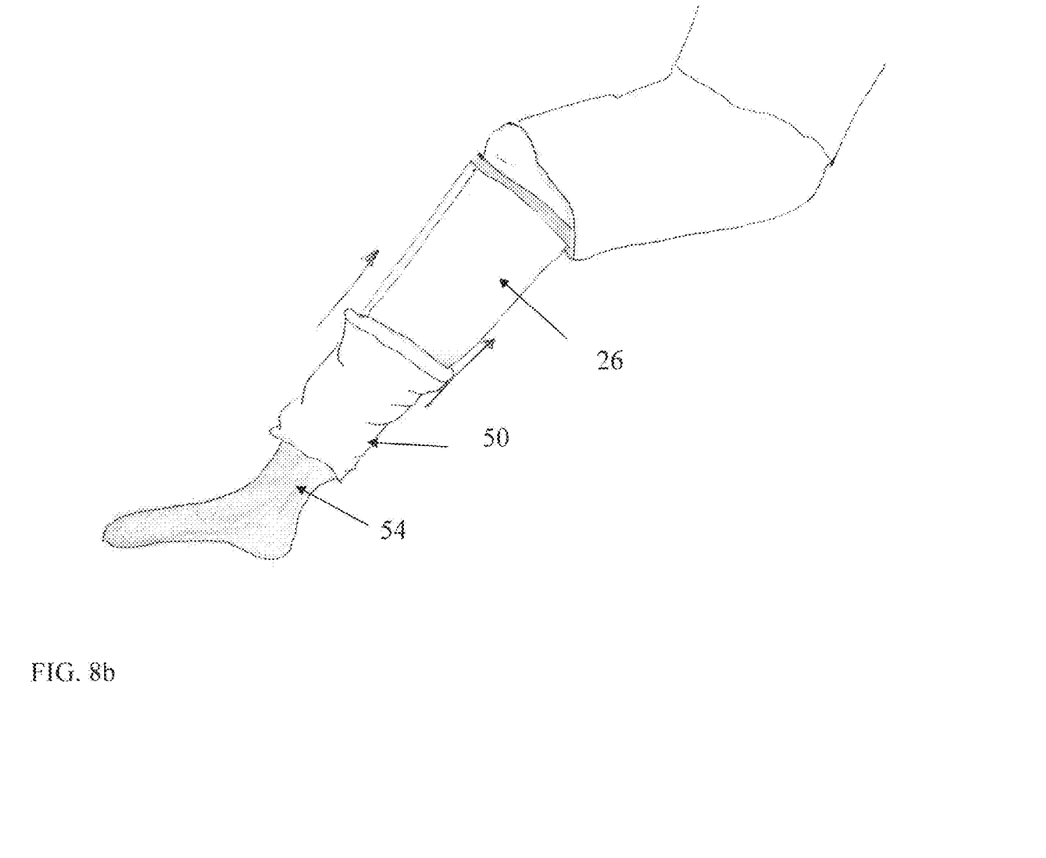
FIG. 8b shows the skin of FIG. 8a being worn by the patient over the calf brace.

Referring to FIG. 8b, the skin cover 50 is rolled on over the brace 26, giving the appearance of human skin and hiding the brace 26. The skin 50 is a life-like covering that is preferably made of silicone. The skin 50 is painted to match the color of the patient's body and may also have small hairs and veins painted on for a more realistic appearance.

Figure 9:
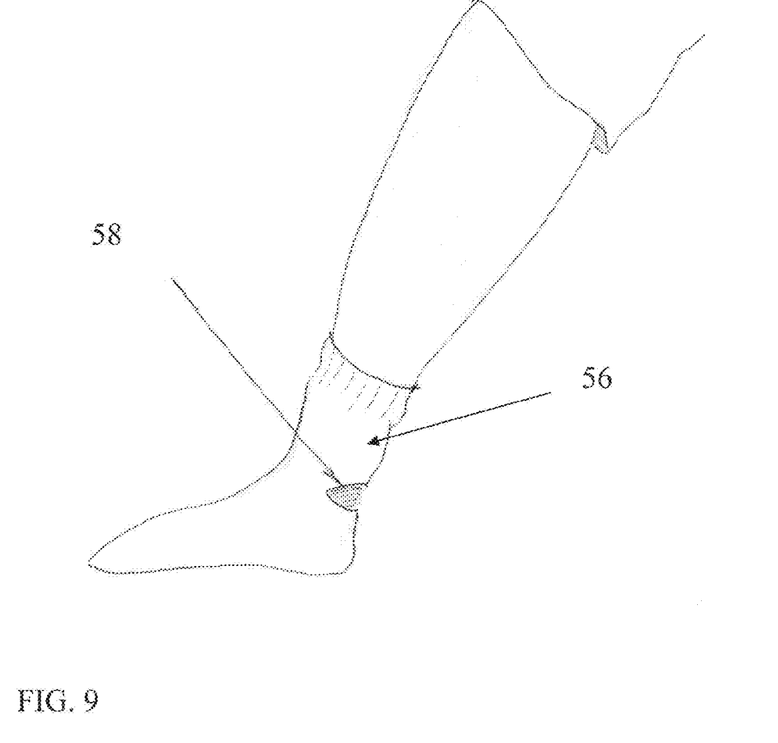
FIG. 9 shows a sock according to an embodiment of the present invention.

Referring to FIG. 9, a sock 56 may be placed on top of the stocking 54 to hide the bottom edge of the calf brace 26 and to provide additional comfort for the patient. According to certain aspects of the preferred embodiment of the present invention, sock 56 has an opening 58 at its rear, and in the center.

Figure 10:
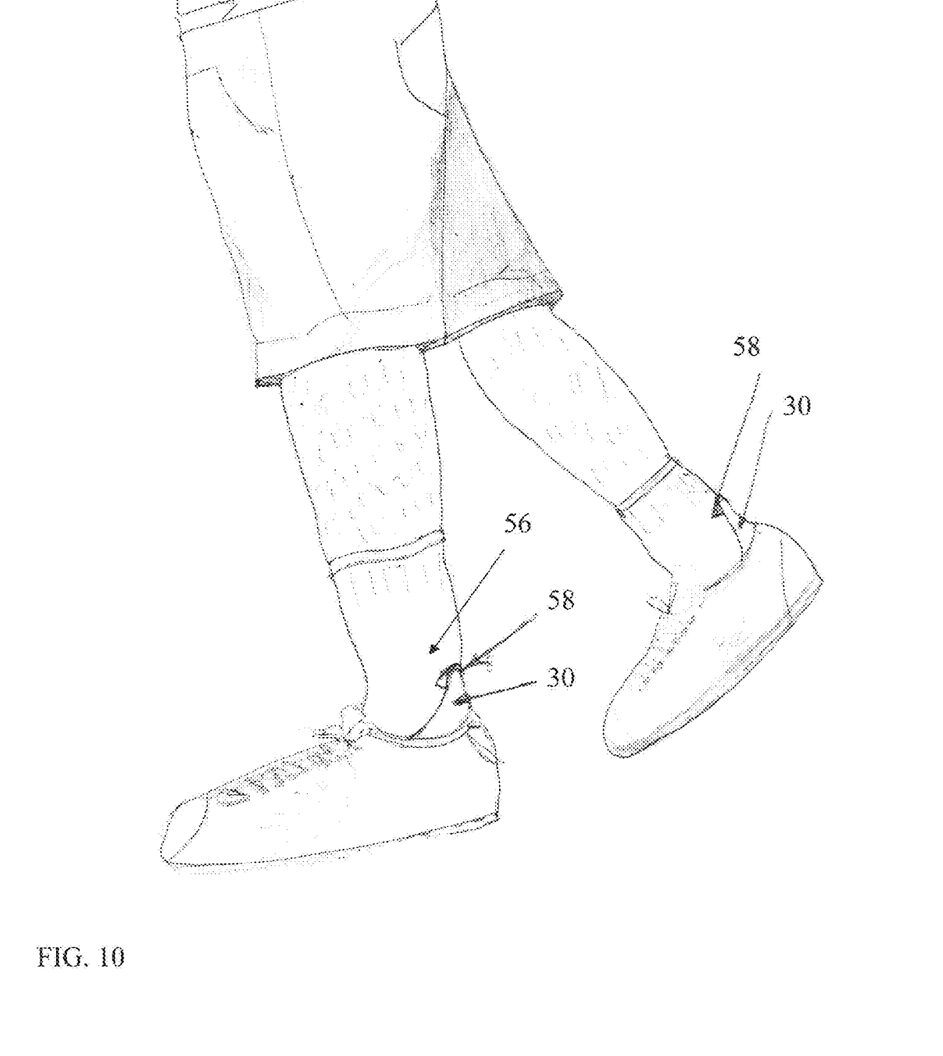
FIG. 10 shows a complete AFO system according to an embodiment of the present invention being worn by a patient.

Referring to FIG. 10, the splint 30 with its footplate 22 can now be attached to the brace 26 by inserting the stalk 24 through the sock opening 58 and into the chute 40. In this way, the patient's skin does not contact the AFO at any point, thereby maximizing comfort while still gaining the benefits of compression and support from the AFO according to an embodiment of the present invention.

It should be noted that the stocking 54, the skin cover 50, and the sock 56 are not necessary for the inventive AFO to work. They are optional components, and are provided to attain maximum comfort together with support and compression.

In the preceding specification, the invention has been described with reference to specific exemplary embodiments thereof. It will however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. An ankle-foot orthosis comprising:
a tubular calf brace substantially enclosing and compressing a calf of a patient and extending from a patient's ankle area to at least a middle portion of the calf when worn by the patient, the tubular calf brace including a rear wall and a chute formed at the rear wall, the chute extending within the tubular calf brace from the patient's ankle area to at least the middle portion of the patient's calf when the tubular calf brace is worn by the patient, the tubular calf brace further including a front wall; and
a splint including a footplate and a stalk extending from the footplate, the stalk being insertable into the chute of the tubular calf brace to removably secure the splint to the tubular calf brace,
wherein the stalk is freely movable within the chute of the tubular calf brace when the splint is removably secured to the tubular calf brace.

2. The ankle-foot orthosis of claim 1, wherein the calf brace further comprises a vertical slit opening located at the front wall.

3. The ankle-foot orthosis of claim 2, further comprising a closing mechanism attached to the vertical slit opening and operable to selectively and securely close the vertical slit opening.

4. The ankle-foot orthosis of claim 1, wherein the calf brace further comprises a core layer having interior and exterior surfaces, an internal silicon layer positioned over the interior surface of the core layer and an external silicon layer placed over the exterior surface of the core layer.

5. The ankle-foot orthosis of claim 2, wherein the core layer, and the internal and external silicon layers have substantially the same height and width, each of the layers being affixed by an adhesive.

6. The ankle-foot orthosis of claim 1, wherein the tubular calf brace is made of an elastic material.

7. The ankle-foot orthosis of claim 1, wherein the chute is lined with a polyethylene terephthalate material over its interior surface.

8. The ankle-foot orthosis of claim 1, wherein the calf brace is shaped like the calf of the patient.

9. The ankle-foot orthosis of claim 1, wherein the calf brace is covered by a skin-like silicon coating.

10. The ankle-foot orthosis of claim 1, further comprising an elastic stocking positionable on the calf of the patient under the calf brace.

11. An ankle-foot orthosis comprising:
a tubular calf brace configured to substantially enclose and compress a calf of a patient, the tubular calf brace including a rear wall and a chute formed at the rear wall, the tubular calf brace further including a front wall;
a splint including a footplate and a stalk extending from the footplate, the stalk being insertable into the chute of the tubular calf brace to removably secure the splint to the tubular calf brace; and
a sock having an opening at its rear, the opening being configured to allow the stalk of the splint to pass therethrough arid into the chute of the calf brace.

* * * * *